United States Patent [19]

Zolecki

[11] Patent Number: 4,571,757
[45] Date of Patent: Feb. 25, 1986

[54] HEAD RESTRAINING DEVICE FOR CERVICAL SUPPORT BRACE

[76] Inventor: Donald L. Zolecki, 159th St. R.R. 6, Box 320, Lockport, Ill. 60441

[21] Appl. No.: 629,520

[22] Filed: Jul. 10, 1984

[51] Int. Cl.[4] .............................................. A61G 1/00
[52] U.S. Cl. ...................................... 5/82 R; 5/434; 5/437; 128/133; 269/328
[58] Field of Search ................. 5/437, 434, 436, 82 R; 269/328; 128/133, 134

[56] References Cited

U.S. PATENT DOCUMENTS

| | | | |
|---|---|---|---|
| 3,469,268 | 9/1969 | Phillips | 5/82 R |
| 3,650,523 | 3/1972 | Darby | 269/328 |
| 3,737,923 | 6/1973 | Prolo | 5/82 R |
| 3,828,377 | 8/1974 | Eary | 5/435 |
| 4,034,748 | 7/1977 | Winner | 5/82 R |
| 4,058,112 | 11/1977 | Johnson | 269/328 |
| 4,124,908 | 11/1978 | Burns et al. | 5/82 R |
| 4,297,994 | 11/1981 | Bashaw | 128/133 |
| 4,400,820 | 8/1983 | O'Dell et al. | 128/133 |

OTHER PUBLICATIONS

"Skull Immobilizer and Positioner", A brochure by E-Z-Em Co., 111 Swalm St. Westbury, N.Y. 11590, 1972, Cat. No. 872.

Primary Examiner—Alexander Grosz
Attorney, Agent, or Firm—Charles F. Lind

[57] ABSTRACT

A device for restraining the head of an injured person carried on a cervical support board, the device having a pair of L-shaped side frames each defining a base portion and a brace portion. The brace portion is sized approximately 6-8 inches long (in the direction of the base portion) and 4-6 inches high (in the direction transverse to the base portion). Velcro-type hook-loop fasteners are fixed to the base portion of the side frames and to the support board where the injured person's head is located. The brace portion of the side frame is adapted then to be snugged against the side of the person's head, extending from close to the neck upwardly beyond the ears; with the base portion then being secured onto the support in this position. Straps are then trained over the person's head, at the forehead and/or chin, and secured again by Velcro-type hook-loop fasteners to the brace portions of the side frames. Openings in the guide portions of the side frames expose the person's ears for visual and touch access thereof; and padding on the brace portion surrounds the access opening to cushion the snugging action against the person's head.

9 Claims, 4 Drawing Figures

U.S. Patent  Feb. 25, 1986  4,571,757
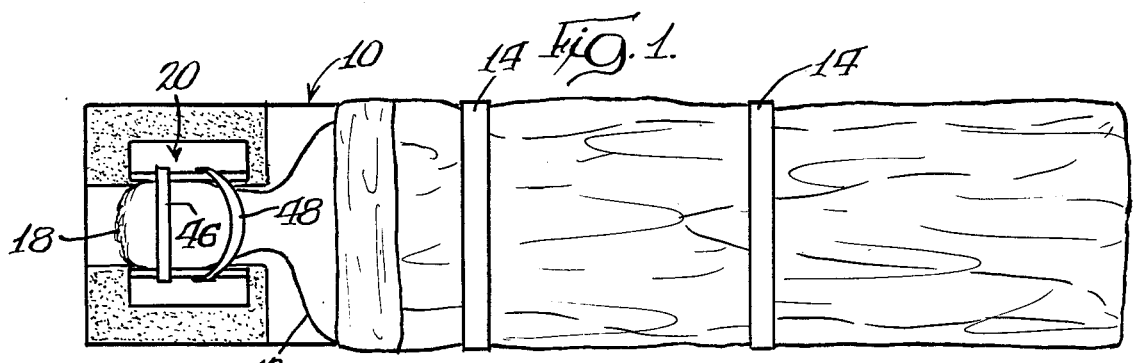
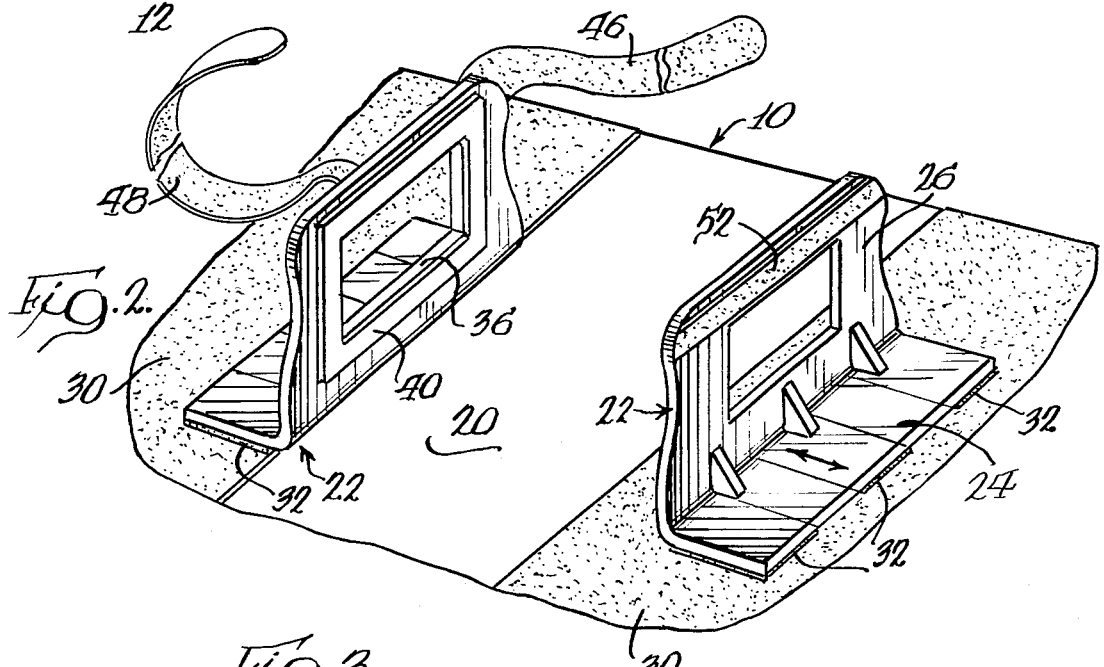
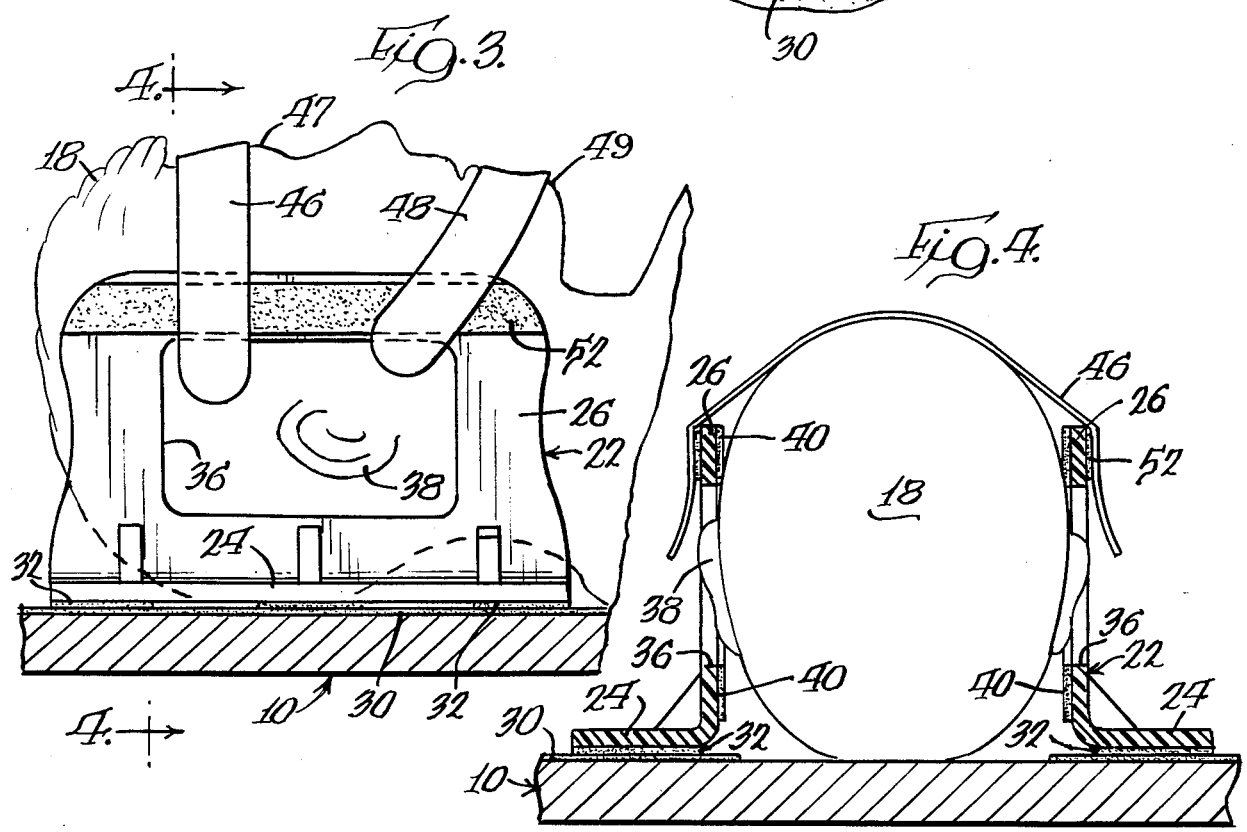

HEAD RESTRAINING DEVICE FOR CERVICAL SUPPORT BRACE

BACKGROUND OF THE INVENTION

Medical people have long appreciated the necessity of restraining the movement of an injured person, particularly one having spinal injuries. For these reasons cervical stabilizing devices utilizing a support board are commonly used to restrain the injured person, particularly during emergency transporting for medical care. The injured person is conventionally strapped to the board with head constraining apparatus also attempting to hold the head in place. The need for head immobilization in many cases is most important, as any single excessive movement can result in paralysis or even death of the injured person.

One form of head restraining device or immobilizer uses a U-shaped pillow that wraps around the head from the top to the two sides. Straps extended from the under side of the board through holes in the board wrap around the sides of the pillow and over the face area of the injured person. This restrains the head from lifting off the board but yet does not prohibit head rotation as the pillows are somewhat compressible. U.S. Pat. No. 4,034,748 issued July 23, 1977 to Steven E. Winner shows a similar type device, except that the pillow comes from the underside of the head and around the sides, where straps again overwrap the face area of the injured party.

U.S. Pat. No. 3,737,923 illustrates upstanding braces adjusted to snug against the sides of the injured person's head. Moreover, a sling type device supported from the brace underlies the person's chin to complete the restrain. However, the braces act against only the top of the head and provide little lateral restrain of the lower chin area of the head so that in fact the person's head can be moved laterally.

U.S. Pat. No. 3,469,268 utilizes a support board with a number of straps designed to overlie the side and face areas of the person's head, generally in the area of the forehead and chin. However this type of support does not prevent rotation of the head.

SUMMARY OF THE INVENTION

A basic object of this invention is to provide a head restraining device for use with a cervical support board to prevent the person's head from being lifted off the board, from being rotated about the axis through the neck, and lastly from being canted about the nect in a side to side manner relative to the plane of the shoulders.

Another object of this invention is to provide a head restraining device that can be quickly and easily used with a minimum of required expertise and/or delay for immobilizing a person's head. In this regard, the subject device has separate side brace components that can be used interchangeably on the left or right side of the injured person, and can be secured with universal width adjustment to snug against the sides of the injured person's head.

Another object of this invention is to provide a head restraining device that can accommodate an extrication collar of the type known as the Philadelphia collar, or others.

Another object of this invention is to provide a head restraining device that can be economically fabricated and mounted in place on a cervical support board and further that can be easily used and cleaned for reuse on subsequent occasions with different injured people. Also, the device can be easily retrofitted to existing support boards, and can be made in different type models for full body board or short board use in extrication from vehicles or the like.

Another object of this invention is to provide a head restraining device that accomplishes all of the above objectives while further provides that the ears of the secured person are exposed and completely accessible to the attending medical technician to aid in the emergency diagnosis and care of the injured person. Also, the subject device can be made without metal parts to allow X-rays to be taken of the injured person through the device itself while it is yet restraining the person's head.

Another object of the invention is to provide a head restraining device that is comfortable in use when functionally restraining the injured person's head.

BRIEF DESCRIPTION OF THE DRAWINGS

FIG. 1 is a top plane view of a cervical restraining board with an injured person strapped in place thereon, and further showing the subject restraining device holding the head of the injured person;

FIG. 2 is a perspective view of the subject head restraining device in place on the cervical support board, except with no head restrained thereby for clarity of disclosure;

FIG. 3 is a side elevational view of the head restraining device shown in operative restraining association with an injured person's head;

FIG. 4 is a sectional view as seen generally from line 4—4 in FIG. 3.

DETAILED DESCRIPTION OF THE INVENTION

The drawings illustrate a cervical support board 10 having an injured person or patient 12 secured thereon by straps 14 over the body portion of the patient. Thus, the patient's body is physically restrained and immobilized, while the head 18 would normally be free and unrestrained. A head restraining device 20 formed according to this invention is used to restrain the head 18 as will now be noted.

The device 20 includes a pair of L-shaped side frames 22 each having a base portion 24 and a brace portion 26. The side frames 22 are designed to be adjustably secured in place with the base 24 flush against the top surface of the constraining support board 10. For this purpose, interfitting Velcro-type hook-loop fasteners are used, preferably with the loop portion 30 being secured to the board 10 and the hook counterpart portion 32 being secured to the underside of the base 24. This allows the two support frames to be fixed to the board 10 with the upstanding brace portions 26 adjustably snugged against the sides of the patient's head (as shown in FIG. 4).

Each of the side frames 22 is extended lengthwise in a direction parallel to the length of the board between 6 and 8 inches, corresponding almost to the average vertical height of a normal adult human head (as shown in FIG. 3). This provides for constraining the head along its entire vertical height, both close to the neck and remote from the neck as well. This is a very important aspect of this invention in that the patient's head is constrained from canting side-to-side about the shoulders as illustrated in FIG. 1.

Another very important aspect of this invention is that the upstanding brace support portion 26 has an opening 36, normally sized significantly larger than the ear 38 of the injured person. This thereby provides exposure of the injured person's ear 38, for visual observation and for touch by an attendant, for diagnostic purposes and/or for administering drugs or medication. Specifically, the ear opening can provide important diagnostic information of the extent of injury by the type and amount of any fluid drainage, so that exposure for sight and touch is helpful. The opening 36 can be 4–6" in the direction of the board 10 and 2–4" in the direction normal to the board.

For added comfort, a padding 40 of foam rubber or the like is provided on the inner face of the upstanding vertical brace portion 26, surrounding the opening 36 and thereby cushioning the snugging action the constraining brace has against the sides of the injured person's head. However, the braces yet provide complete support of the person's head.

Separate straps 46 and 48 would commonly be used respectively over the forehead 47 and over the chin 49 of the person's head. The straps are secured to the outside face of each upstanding brace portion 26, as again by means of mating Velcro-type hook-loop fasteners. In this regard, a strip 52 of the hook portion can be extended across the top of each brace portion 26, and the straps 46 and 48 can be formed of the loop portion. The straps 46 and 48 when secured in place across the forehead and chin respectively hold the upstanding brace portions 26 snugged against the sides of the person's head for firm stable support. The upstanding brace portion 26 can be made 4–6" high, operable to extend above the board beyond the center part and ears 38 of the average adult person's head.

The side frames 22 would be formed of a durable material, such as plastic, which would further be washable for reuse. Likewise the Velcro-type fastener means formed on the side frames, on the straps, and on the support board itself would be washable. As noted, since these components are devoid of metals, X-rays can be taken of the head and neck regions of the injured person through the restraining device, while the latter may yet be holding the person's head stable.

As shown, the Velcro-type fastener 30 can extend over the side margins of the support board to allow for a wide range of adjustment where the side frames 22 can be secured in place thereon. Likewise, the Velcro-type fastener can extend generally in spaced narrow rows 32 over the base portion 24 of the side frames or it can in an alternate embodiment (not shown) be made to cover the entire base portion.

The separate straps 46 and 48, and the side frames 22, can be easily removed when desired to release the patient from the restrain of the board. This is done with a pulling type separating action of the straps, initially from one of the loose ends; and by canting the top edge of the brace section 26 in the direction away from the person's head.

The entire restraining device 20 would be easily fabricated in its initial form, can be readily used without special expertise or skills, and restrains the person's head from lifting off the board, from rotating relative to the board, or from canting relative to the body of the injured.

What is claimed is:

1. For use with a cervical support board in moving an injured person strapped to the board, a head restraining device comprising the combination of:
   a pair of L-shaped substantially rigid side frames each having a generally flat base portion and a brace portion angled tranversely thereto,
   means for fixedly securing the base portion of each side frame to the board with brace portions then being adjacent and adjustably snugged against the sides of the injured person's head on the board,
      said securing means includes having mating Velcro-type hook-loop fasteners fixed to the side frame and to the board,
   strap means adapted to overlie the injured person's head and means to secure the strap means to the brace portions of the side frames for thereby restraining the head against the board,
   each of the brace portions having an opening therein operable to line up with the person's ears,
   padding located on the head side of each brace portion adjacent the access opening therein operable to engage the person's head and cushion the snubbing action the brace portions have thereagainst, and
   each brace portion opening being significantly larger than the person's ear operable not only to line up with the person's ears but also to provide both visual exposure of and physical access to the ear.

2. A head restraining device according to claim 1, wherein each side frame is elongated in the direction of the board adapted to be positioned snugged against the sides of the injured person's head and to extend then from close to the neck to remotely of the neck.

3. A head restraining device according to claim 2, wherein the brace portion of each side frame is elongated to be between 6 and 8 inches operable to correspond almost to the average height of a human head and thereby extend lengthwise along almost the full height of the person's head.

4. A head restraining device according to claim 1, wherein the brace portion of each side frame is operable to upstand from the board, when the side frame is secured to the board, a distance forwardly beyond the center part and ears of the injured person's head.

5. A head restraining device according to claim 4, wherein the brace portion of the side frame is made 4–6 inches high.

6. A head restraining device according to claim 1, wherein the means to secure the strap means to the base portions include having mating Velcro-type hook-loop fasteners fixed to the side frame and to the strap, the loop part of the fastener being fixed to the strap, and the hook part of the fastener being fixed to the brace portion of the side frame.

7. A head restraining device according to claim 6, wherein the hook part of the Velcro-type fastener is fixed to the brace portion of each side frame on the side thereof opposite from the person's head and adjacent the access opening formed in the brace portion.

8. A head restraining device according to claim 1, wherein the means for securing the base portion of the side frame to the board includes having the loop part of the hook-loop fasteners being fixed to the board and the hook part of the fasteners being fixed to the base portion of the side frame.

9. A head restraining device according to claim 1, wherein the head restraining device components are devoid of metal materials, operable to allow X-rays to be taken of the injured person through the device.

* * * * *